United States Patent [19]

Jensen et al.

[11] Patent Number: 5,753,467
[45] Date of Patent: May 19, 1998

[54] METHOD FOR THE IDENTIFICATION OF MICROORGANISMS BY THE UTILIZATION OF DIRECTED AND ARBITRARY DNA AMPLIFICATION

[75] Inventors: Mark Anton Jensen, West Chester, Pa.; Neil Alexander Straus, North York, Canada

[73] Assignee: E. I. du Pont de Nemours and Company, Wilmington, Del.

[21] Appl. No.: 701,290

[22] Filed: Aug. 22, 1996

Related U.S. Application Data

[63] Continuation of Ser. No. 281,496, Jul. 27, 1994, abandoned, which is a continuation of Ser. No. 803,302, Dec. 4, 1991, abandoned.

[51] Int. Cl.$^6$ ............................. C12Q 1/68; C12P 19/34
[52] U.S. Cl. ............................. 435/91.2; 435/6
[58] Field of Search .......................... 435/6, 91.2

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,885,697 | 12/1989 | Hubner | 364/497 |
| 4,965,188 | 10/1990 | Mullis et al. | 435/6 |
| 5,437,975 | 8/1995 | McClellan et al. | 435/6 |
| 5,487,985 | 1/1996 | McClelland | 435/91.2 |
| 5,523,217 | 6/1996 | lupski et al. | 435/91.2 |
| 5,574,145 | 11/1996 | Barry et al. | 536/24.32 |

FOREIGN PATENT DOCUMENTS

| | | | |
|---|---|---|---|
| 297 379 | 1/1989 | European Pat. Off. | C12Q 1/68 |
| 335 633 | 10/1989 | European Pat. Off. | C12Q 1/68 |
| 395 282 | 10/1990 | European Pat. Off. | C12Q 1/68 |
| 414 469 | 2/1991 | European Pat. Off. | C12Q 1/68 |
| WO 91/14003 | 9/1991 | European Pat. Off. | C12Q 1/68 |
| WO 92/14844 | 3/1992 | European Pat. Off. | C12Q 1/68 |
| 0332435 | 4/1992 | European Pat. Off. | C12Q 1/68 |
| WO 92/08117 | 5/1992 | European Pat. Off. | C12Q 1/68 |
| 2636075 | 9/1990 | France | C12Q 1/68 |
| WO 89/10414 | 2/1989 | WIPO | C12Q 1/68 |

OTHER PUBLICATIONS

Jensen et al., Appl. Env. Micro. 59(4), 945–952 (1993).
Barry et al., PCR Methods and Applications, 1:51–56, 1991.
Williams et al., Nucleic Acid Research, 18(22), 6531–65.
Welsh et al., Nucleic Acid Research, 18(24), 7213–7218.
Vilgalus et al., A. Bact., 4238–4246, 1990.
Dams et al., Compilation of Small Ribosomal Subunit RNA Sequences, Nucleic Acids Research, 16, r87.
Gutell et al., A Compilation of Large Subunit RNA Sequences Presneted in a Structural Format, Nucleic Acids Research, 16, Supplement, R175.
Innis et al., PCR Protocols, A Guide to Methods and Applications, Academic Press, 3–12, 1989.
Versalovic et al., Nucleic Acids Research, 19 No. 24, 6823–6831.
Candrian et al., Molecular and Cellular Probes, 6, 13–19, 1992.
Maniatis et al., Molecular Cloning—A Laboratory Manual, Cold Spring Harbor Laboratory, 161, 1982.
Sommer et al., Minimal Homology Requirements for PCR Primers, Nucleic Acids Research, 17(16), 6749, 1989.
Liang et al., Differential Display of Eukaryotic Messenger RNA By Means Of The Polymerase Chain Reaction, Science, 257, 967–971, 1992.

*Primary Examiner*—Kenneth R. Horlick

[57] ABSTRACT

A method for the identification of microorganisms is disclosed, comprising first isolating genomic DNA from the suspect microorganism. The isolated DNA has variable sequences interspersed between highly conserved rDNA sequences. The variable sequences are amplified. The amplification reaction is carried out in such manner as to either amplify the variable sequences interspersed between highly conserved rDNA sequences or to amplify arbitrary genomic regions in conjunction with the variable sequences. The resulting amplified DNA fragments are polymorphic with respect to both size and number in a manner which is specific to species, serotype and strain. The distribution of the polymorphic fragments is analyzed and compared to an established database to determine the species, serotype and strain of the suspect microorganism.

11 Claims, 10 Drawing Sheets

HYPERVARIABLE SPACER REGIONS

METHOD FOR THE IDENTIFICATION OF MICROORGANISMS BY THE UTILIZATION OF DIRECTED AND ARBITRARY DNA AMPLIFICATION

This is a continuation of application Ser. No. 08/281,496, filed Jul. 27, 1994, abandoned, which is a continuation of application Ser. No. 07/803,302, filed Dec. 04, 1991, abandoned.

FIELD OF THE INVENTION

The present invention relates to the field of microbial identification using DNA amplification. More particularly, the present invention relates to the identification of species of prokaryotic organisms, based on a characterization of products generated by amplification of specific genomic regions significant to the organism. In addition by amplification of arbitrary sections of the genome in conjunction with the amplification of specific genomic regions, identification of species, serotype and strain of the microorganism is achieved.

BACKGROUND OF THE INVENTION

A variety of literature and references have been recently published pertaining to the identification of microorganisms such as bacteria in suspect samples. In these materials much emphasis has been placed on developing procedures to identify or classify microorganisms using a presumptive basis. That is, the researcher employs the technology to screen for a particular microorganism or pathogen of interest. Still other references require laborious screening with a variety of specific primers or incorporate varieties and carefully controlled operating constraints. As will become apparent from the ensuing discussion, the present invention obviates these disadvantages.

PCT Publication WO89/10414 to Wallace et al. discloses a process for the creation of new genetic markers and the determination of multiple genetic markers. A genomic DNA sample is amplified, and the sequence variation within the amplified fragment is detected. The amplified fragments are then detected. This publication teaches a general concept wherein a polynucleotide target sequence including a plurality of polymorphic loci are amplified, with the product analyzed for the presence or absence of target sequences having the locus specific characteristic. However, Wallace et al. do not focus on the amplification of spacer regions interspersed between highly conserved rDNA sequences for detecting microorganisms. The reference does not address this approach either alone or together with arbitrary regions from the entire genome.

EP 0 332 435 is directed to a method of detecting one or more variant nucleotide sequences. The nucleic acid sample is contacted with a diagnostic primer substantially complementary to a diagnostic portion of a target base sequence. Extension only occurs where a terminal nucleotide of the primer is complementary to a variant or normal nucleotide of the target base sequence. The extension product if any is detected. This approach does not target the spacer regions interspersed between conserved rDNA sequences for amplification and subsequent analysis, as presently contemplated.

Williams et al., "DNA polymorphisms amplified by arbitrary primers are useful as genetic markers", Nucleic Acid Research, Vol. 18, No. 22 p. 6531–6535 and Welsh et al., "Fingerprinting genomes using PCR with arbitrary primers", Nucleic Acid Research, Vol. 18, No. 24 p. 7213–7218, both demonstrate the use of arbitrary primers in a DNA amplification reaction to generate a characteristic pattern of amplification products from genomic DNA from a variety of sources including bacteria. The approach used by Williams et al. employs small primers run at relatively high stringency conditions. The polymorphisms are called Random Amplified Polymorphic DNA (or RAPD) markers, and are useful to construct genetic maps in a variety of species. Welsh et al. describe the use of longer primers in an amplification process which uses low stringency conditions in the early cycles followed by higher stringency conditions in the later cycles. In both cases, bacterial strains are identified by comparison of the arbitrarily primed genomic print with predetermined reference patterns.

The procedures described by Williams et al. and Welsh et al. both employ the use of arbitrary primers with a relatively high number of amplification cycles. Significant levels of formation of secondary amplification products and nonspecific DNA synthesis frequently result from amplifications run under these conditions. These amplification products are separated by electrophoresis and the resulting pattern is then analyzed and processed by pattern recognition software.

Amplification with a single arbitrary primer, such as is described by Williams et al. and Welsh et al. may yield an arbitrary product pattern which possesses both common elements at the level of species and differentiated elements at the level of strain for a given species. However, a single arbitrary primer or pair of arbitrary primers may not demonstrate this property across a broad spectrum of microorganisms. Hence, different species of microorganisms may require a diverse menu of arbitrary primers to achieve common pattern elements at the level of species and differentiated elements at the level of strain. The present invention represents an improvement over the procedures described by Williams et al. and by Welsh et al. in that it does not require screening unknown microorganisms with a battery of possible primers or making a presumptive preliminary identification.

French Patent No. 2,636,075 concerns the detection of bacteria, yeasts, parasites and other eukaryotic microorganisms in, for example, food products. Ribosomal RNA if any is extracted from the product, and transcribed to DNA in the presence of reverse transcriptase. The DNA strand is transcribed to a complementary strand in the presence of primers, and then amplified in the presence of one or more primers which define a known detectable sequence. The amplified sequence is detected by electrophoresis in an acrylamide gel or by hybridization using probes which cover in part the amplified region.

Vilgalys et al., "Rapid genetic identification and mapping of enzymatically amplified ribosomal DNA from several Cryptococcus species", Journal of Bacteriology, August 1990, p. 4238–4246, describe a simplified procedure for performing the restriction typing and mapping necessary to identify related species of pathogenic fungi. An approach which uses a polymerase chain reaction (as below) to amplify a known region of ribosomal DNA followed by a restriction digest and electrophoretic separation is discussed.

The identification procedures described in French Patent No. 2,636,075 and by Vilgalys et al., both employ multiple enzymatic processing steps which require purification of the intermediate products. Both the multiplicity of enzymatic steps and the necessity for intermediate product isolation make these methods expensive and labor intensive. Mullis et al., U.S. Pat. No. 4,683,195, and Mullis, U.S. Pat. No. 4,683,202 disclose polymerase chain reactions (referred to as the PCR procedure) which can be used to amplify any specific segment of a nucleic acid. These analytical methods have been used to detect polymorphisms through amplification of selected target DNA segments from test genomes. A drawback to such methods is the requirement that a sufficient number of bases at both ends of the specific segment be known in sufficient detail so that two oligonucleotide primers can be designed which will hybridize to different strands of the target segment. It is labor intensive to obtain the necessary sequence information from target genomes in order to design the necessary primers.

It is an object of the present invention to provide a method for microbial identification at the level of genus and species by the detection of variations in length and number of fragments located between highly conserved rDNA sequences. These fragments are referred to as Ribosomal Sequence (RS) fragments. It is a further object of the present invention to provide a method for microbial identification using the preferred PCR procedures. It is a further object of the present invention that only a single pair of nucleic acid sequences will be required for the amplification which provides the basis for the method of microbial identification. To achieve this end, the variations in the aforementioned RS fragments are characterized by amplification of variable sequences (as spacer regions) interspersed between regions known to contain highly conserved sequences (as rDNA sequences). These DNA sequences may flank the variable sequences or may otherwise be located in relation to the variable sequences. It is yet a further object of the present invention that the identification is extended to the level of serotype and strain through modifications which facilitate the amplification of additional arbitrary regions of the microbial genome in conjunction with the amplification of the variable sequences interspersed between the highly conserved rDNA sequences. A feature of the present invention is its compatibility with various other techniques common to microbiological and molecular biological efforts, including but not limited to electrophoresis and staining (as by ethidium bromide) or spectrophotometric procedures.

It is an advantage of the present invention that the same pair of primers are used for all species of microorganism to generate amplification products. Since the sequences of these primers are highly conserved among prokaryotic organisms these primers are generically applied. Amplification from this single pair of primers generates products from conserved sequences in a known genetic locus which are characteristic of a given species. Additional products are generated by the arbitrary amplification events and are used to differentiate strains within a species. A substantial savings of time and expense is realized because the necessity for screening or presumptive identification has been eliminated.

It is another advantage of the present invention that use of the method recited herein yields a pattern upon electrophoretic separation of the reaction products, which contains a minimal amount of secondary and nonspecific amplification products. These patterns are more amenable to analysis and processing by the types of pattern recognition software which are used for pattern comparison with a reference data base such as is described in U.S. Pat. No. 4,885,697.

It is yet another advantage of the present invention that the method recited herein requires only a single enzymatic processing step with no subsequent sample purification prior to electrophoretic separation. As such, the method is not labor intensive and results in a significant savings of time.

These and other objects, features, and advantages of the present invention will become more readily understood upon having reference to the following description of the invention.

SUMMARY OF THE INVENTION

Described herein is a method for the identification of the species of a microorganism. This method comprises:

(a) isolating genomic DNA from the microorganism, said genomic DNA comprising variable sequences interspersed between highly conserved sequences;

(b) amplifying said variable sequences thereby producing fragments having particular distributions in size and number; and (c) separating said fragments by size and analyzing the distribution of said fragments thereby determining the species of the microorganism.

Further described herein is a method for the identification of the species, serotype and strain of a microorganism comprising:

(a) isolating genomic DNA from the microorganism, said genomic DNA comprising variable sequences interspersed between highly conserved sequences in addition to arbitrary regions along the genome thereof;

(b) amplifying said variable sequences thereby producing fragments having particular distributions in size and number;

(c) amplifying said arbitrary regions thereby producing Arbitrary Genomic (AG) fragments having particular distributions in size and number simultaneously with (b); and (d) separating said fragments and said AG fragments by size and analyzing the distribution of said fragments and said AG fragments thereby determining the species, serotype and strain of the microorganism.

These methods are particularly useful for determining species, serotype and strain of bacteria, such as are resident as food borne microorganisms.

In the preferred embodiment, the highly conserved sequences are highly conserved rDNA sequences. Hence the fragments are RS fragments.

According to a preferred embodiment of the methods disclosed herein, step (a) isolation comprises cellular lysis and deproteinization. Further, step (b) amplification may preferably comprise annealing at least one pair of oligonucleotide primers to the highly conserved rDNA sequences. A nucleic acid polymerase and nucleotide triphosphates are introduced to the primers, suitable to amplify the variable sequences interspersed between the highly conserved rDNA sequences. Alternatively the oligonucleotide primers are annealed to the aforementioned sequences and to a plurality of arbitrary regions, ensuring suitable amplification of the arbitrary regions.

DETAILED DESCRIPTION OF THE FIGURES

Figure 6:
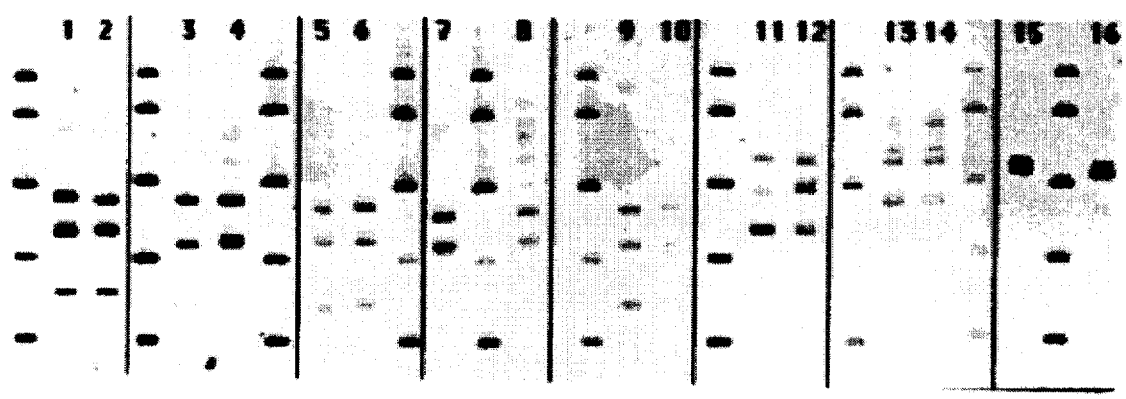

FIG. 6 is the visualized pattern for the amplification products of the spacer region in the rRNA genetic locus for eight additional species taken from four genera which are related to the pathogenic species of interest. These species are as follows: *Citrobacter freundii, Citrobacter diversus, Enterobacter aerogenes, Enterobacter agglomerans, Enterobacter cloacae, Proteus mirabilis, Proteus vulgaris* and *Yersinia enterocolitica*.

Figure 7:
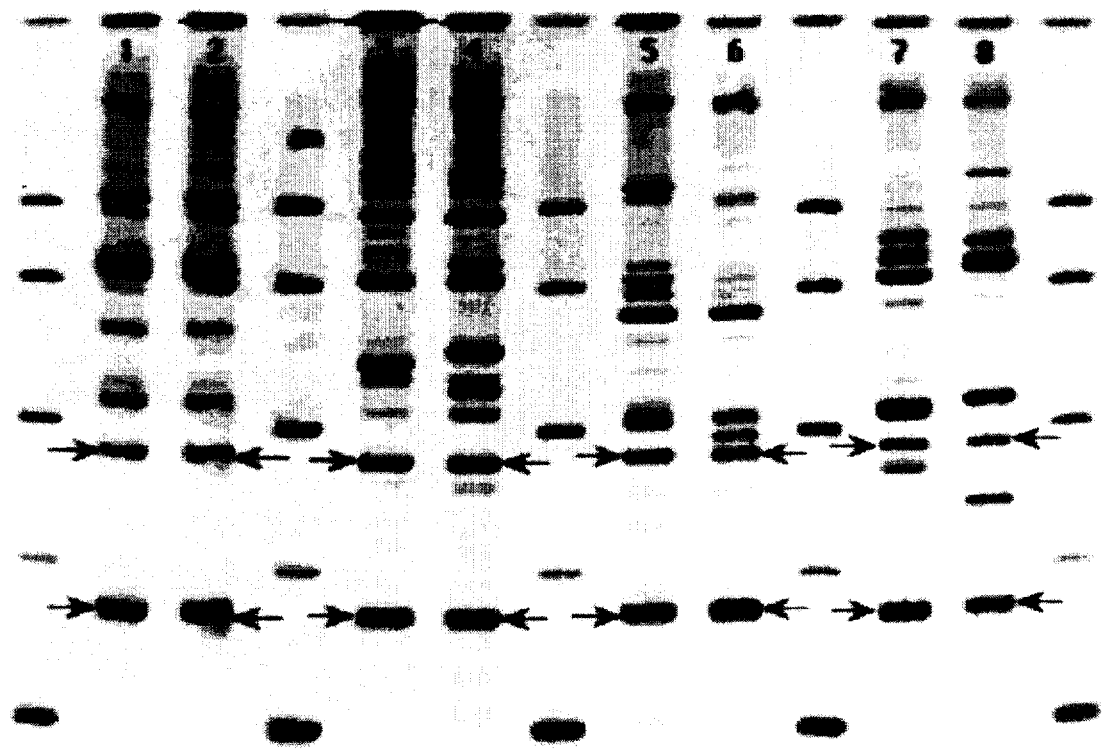

FIG. 7 is the visualized pattern for the amplification products of both the spacer region in the rRNA genetic locus and tentirbitrary regions from the entire microorganism genome for three species from the genus Listeria including *Listeria monocytogenes*.

Figure 8:
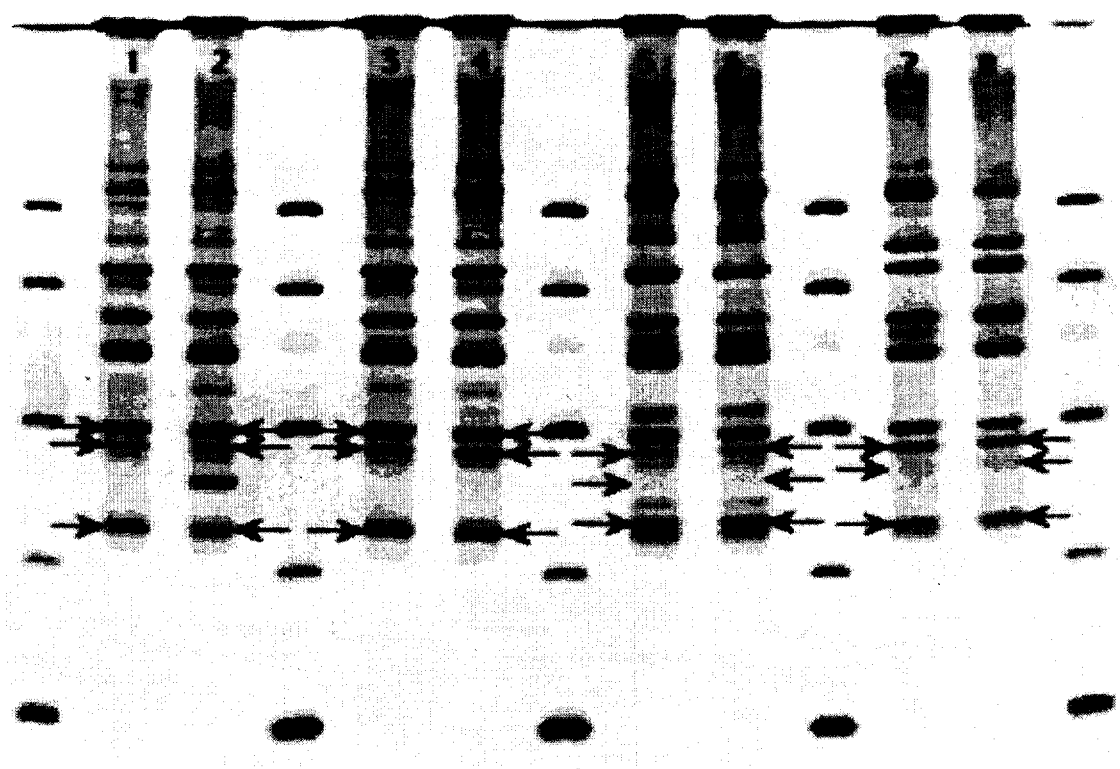

FIG. 8 is the visualized pattern for the amplification products of both the spacer region in the rRNA genetic locus and the arbitrary regions from the entire microorganism genome for three serotypes from the genus Salmonella including *Salmonella typhimurim*.

Figure 9:
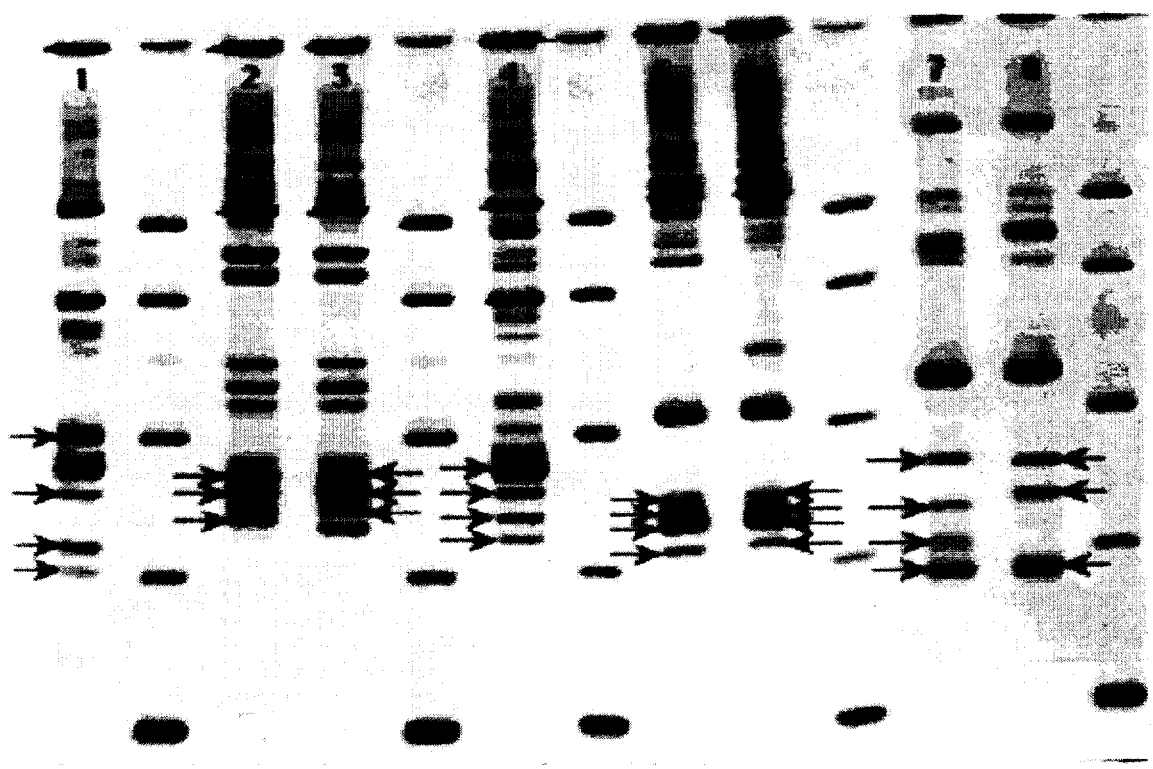

FIG. 9 is the visualized pattern for the amplification products of both the spacer region in the rRNA genetic locus and the arbitrary regions from the entire microorganism genome for three species from the genus Staphylococcus including *Staphylococcus aureus*.

Figure 10:
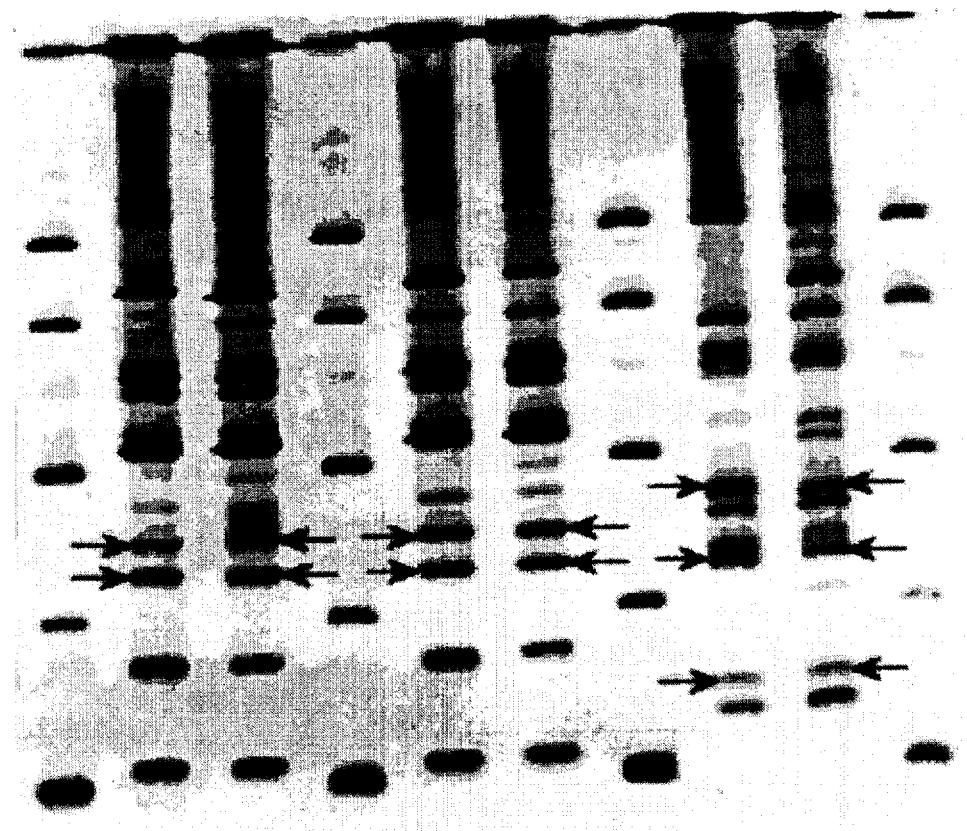

FIG. 10 is the visualized pattern for the amplification products of both the spacer region in the rRNA genetic locus and arbitrary regions from the entire microorganism genome for four strains of *Escherichia coli* and two strains of *Citrobacter freundii*.

DETAILED DESCRIPTION OF THE INVENTION

The method described herein is useful in identifying a wide variety of microorganisms. Representative but not exhaustive of the many types of organisms including both genus, species and serotype that may be elicited through the use of the present procedures are *Listeria monocytogenes, Listeria welshimeri, Listeria innocua, Listeria ivanovii, Salmonella typhimurium, Salmonella enteritidis, Salmonella newport, Salmonella infantis, Staphylococcus aureus, Staphylococcus scuiri, Staphylococcus warneri, Staphylococcus saprophyticus, Staphylococcus epidermidus, Escherichia coli, Escherichia fergusonii, Escherichia blattae, Escherichia hermanii, Escherichia vulneris, Citrobacter freundii, Citrobacter diversus, Enterobacter aerogenes, Enterobacter agglomerans, Enterobacter cloacae, Proteus mirabilis, Proteus vulgaris,* and *Yersinia enterocolitica*. Such a listing may form a database of previously visualized products which when compared to the electrophoresed, visualized fragment products according to the present method, afford an identification of the species (and the serotype and strain if applicable).

It is readily appreciated by one skilled in the art that the present method may be applied to microorganisms in the context of a wide variety of circumstances. Thus, a preferred use of the present invention is in the identification of microorganisms in food. Additionally, research directed to microbial infections in humans, other animals and plants would benefit from the procedure herein.

Figure 1:
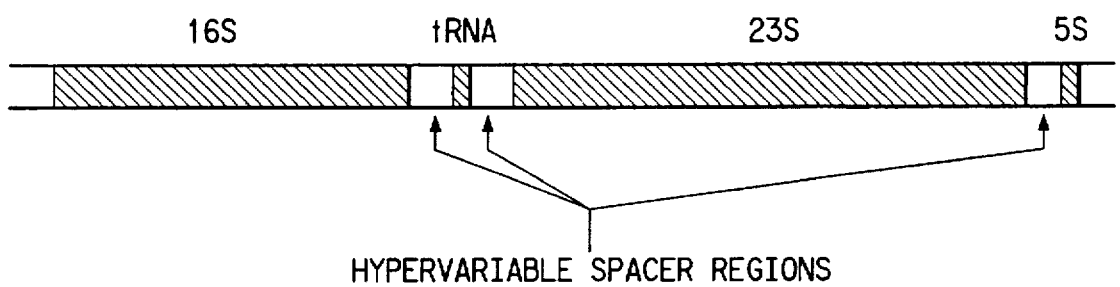
FIG. 1 is a generalized schematic of the rRNA genetic locus of bacteria. This locus contains the conserved sequence regions where the priming for the amplification occurs and the spacer region between these priming sites.

The present invention relates to the identification of species of prokaryotic organisms, based on a characterization of products generated by amplification of the spacer region found between the 16S and 23S regions of the rRNA genetic locus. The rRNA genetic locus is a genetic unit which is found in prokaryotic cells. Significant portions of the nucleic acid sequence which make up this genetic locus are common to all prokaryotic organisms. (FIG. 1 showns a generalized schematic of this locus.) The overall relatedness of the 16S, 23S, and 5S regions of this genetic locus has been used as a tool to classify differing species of prokaryotes. Genes coding for the 16S ribosomal RNA region have been shown to contain regions of highly conserved sequences which are interspersed between areas of less conserved sequences. Although less well characterized than the 16S region the 23S ribosomal RNA region has also been shown to have a similar makeup.

The 16S, 23S and 5S gene sequences are separated by spacer units. These spacer units (also referred to as spacer regions) exhibit a large degree of sequence and length variation at the levels of genus and species for prokaryotic organisms. Within a single genome of a given species there are frequently multiple rRNA genetic loci present. The spacer regions found within these loci also show a significant degree of variation in length and sequence. It has been shown that conserved sequences of the 16S region can be used as sites for amplification of nonconserved sequences within the 16S region for the purpose of determining their nucleotide composition. Similarly, it is reasonable to expect that conserved regions on the 3' and 5' ends of the 16S and 23S rDNA, respectively, can be used as priming sites for the amplification of the spacer unit contained between these two conserved regions. It is expected that amplification of such spacer regions will produce fragments whose size and number is characteristic of a given species of prokaryote.

The 16S regions of rRNA genetic loci have been sequenced for a broad range of bacteria. A compilation of this sequence data is given in Dams et al., "Compilation of small ribosomal subunit RNA sequences", Nucleic Acids Research, Vol. 16, supplement, p. r87. This sequence data was examined for the purpose of identifying a highly conserved sequence in the 16S region immediately adjacent to the spacer region. The sequence which was chosen was GAAGTCGTAACAAGG (SEQ ID No:1) which will be designated as P1. This sequence lies in a highly conserved region approximately 30–40 bases away from the spacer region.

There is substantially less sequencing data available for the 23S region. Gutell et al., "A compilation of large subunit RNA sequences presented in a structural format", Nucleic Acids Research, Vol. 16, supplement, p. r175 present a small collection of 23S sequences consisting of five bacterial and four plant chloroplast sequences. The second primer chosen represented the most conserved sequence among the bacterial sequences presented which could be found immediately following the spacer region. The sequence which was chosen was CAAGGCATCCACCGT (SEQ ID NO:2) which will be designated P2. This sequence was conserved among the five bacterial examples cited and was located approximately 20 bases away from the spacer region. The fact that this sequence also matches the plant chloroplast sequence in the same region for thirteen of fifteen bases (87% similar) gives additional reason to expect that this particular sequence is evolutionarily stable and likely to be conserved over a broad spectrum of bacteria.

Primers for both the 16S and 23S regions were limited to seventeen bases in length (and it is preferable to use 15–17 bases) because longer primers would extend into regions of more poorly conserved sequence. Primers which overlap regions that are not conserved among all bacteria are expected to show more variation in amplification efficiency. This would make it more difficult to specify a single set of primers and amplification conditions for all bacterial genomic DNA samples. It is possible that some sequences which are not ribosomal spacers may be amplified by the primer set of P1 and P2. This type of occurrence is expected to be rare but amplification of nonspacer sequences even under highly stringent conditions can not be ruled out. Such an amplification does not detract from the utility of the method and will likely provide additional pattern information for the differentiation of microorganisms below the species level. Any of the amplified fragments produced by the high stringency amplification with primers P1 and P2 will be referred to as RS fragments. This name serves to indicate that the sequences for these primers was taken from highly conserved rDNA sequences flanking a ribosomal spacer region.

It is frequently necessary to carry the identification of pathogenic species beyond the level of species to serotype and strain. This information is valuable, for example, in identifying the source of food contamination and in tracing the course of epidemic infections. Although the patterns generated from the amplification of the spacer regions in the rRNA genetic locus contain sufficient information to identify species, they do not always contain sufficient information to carry the identification to the level of serotype and strain. Ribosomal RNA genes constitute only about 1% of the total prokaryotic genome. In order to identify species at the serotype and strain level, we need to gather additional information relating to the genomic composition of those areas located outside the rRNA genes.

A procedure for generating arbitrary amplification fragments from genomic material has been demonstrated by Williams et al. The approach describes the use of a small oligonucleotide, i.e., approximately 10 bases, of arbitrary composition in a DNA amplification reaction. Short primers are used in order that complementary and reverse complementary sequences to the primer can be found at distances along the genome which are sufficiently small that DNA amplification can take place. The fragments generated in the amplification process are called Random Amplified Polymorphic DNA RAPD markers. These RAPD markers show a size distribution which is sensitive to modest differences in the genomic makeup of the DNA used in the amplification process.

In the present invention we provide a method for the generation of arbitrary amplification fragments from the genome of the target microorganism in conjunction with the generation of amplification fragments from the spacer regions in the rRNA genetic locus. Amplification of the putative rDNA spacer regions is achieved using 15–17 base primers and annealing temperatures of up to about 72° C. (and preferably up to about 55° C.) for a duration of about 1–20 (preferably about 2–10) minutes in the amplification reaction. Differentiation of species at the serotype and strain level is achieved by reducing the size of the primers used in the amplification, while still maintaining the conserved element of their sequence. By decreasing the size of the primers to 11 bases in length (and it is preferable to use 10–12 bases) and reducing the annealing temperature to 43°–46° C. for a duration of about 1–10 minutes (preferably about 5–10 minutes), it is possible to generate both RS fragments and RAPD markers from the genomic DNA using a single pair of primers. Since the RAPD markers are generated by amplification of arbitrary genomic sequences they will be referred to as AG fragments. The combined amplification of RS and AG fragments will be referred to as RS/AG amplification. The RS fragments which are produced in the amplification reaction are sufficiently distinct to permit differentiation of microorganisms at the level of species. The additional AG fragments which are generated provide sufficient additional diversity to differentiate microorganisms at the serotype and strain level.

It is an important feature of this invention that each RS/AG amplification pattern contains RS fragments which can be used to identify species. This means that unique strains of a given species will contain common pattern elements which will indicate that the strains are derived from a common species. When a strain is encountered which is not represented in the reference pattern database, the species of the strain can still be identified providing that the RS fragments for that species are contained in the reference pattern database.

In order to perserve the conserved nature of the primers used to generate the RS/AG pattern the 11-base primers used in the amplification reaction are a subset of the 15-base primer sequences. The sequence which was chosen for the 16S area adjacent to the spacer was GAAGTCGTAAC (SEQ ID NO:3), which will be designated as P3. The sequence which was chosen for the 23S area following the spacer region was AAGGCATCCAC (SEQ ID NO:4), which will be designated P4.

A significant degree of intramolecular hybridization is known to occur within the rDNA genetic locus. The resulting secondary structure frequently makes it difficult for amplification primers to compete for hybridization sites. In order to enhance the amplification of fragments contained within the rDNA region it is necessary to modify the amplification temperature profile which is typically practiced. The principal modifications consist of the use of substantially longer annealing times. Seven minutes is used for P1 and P2 for the generation of the RS fragments. Eight minutes is used with P3 and P4 to generate both RS and AG fragments in a single reaction. In both cases, amplification reactions are being run under high stringency conditions in conjunction with a decreased number of amplification cycles. A high stringency amplification is accomplished by running the reaction at the highest annealing temperature where products are reproducibly formed. For the primer set P1 and P2 the maximum temperature which yielded reproducible product formation was 55° C. For the primer set P3 and P4, the maximum temperature which yielded reproducible product formation was 43° C. Use of maximum annealing temperature insures that only the most stable hybridization structures will form and that the areas surrounding the priming sites will possess a minimal amount of secondary structure.

There are two reasons for the use of a long annealing time in the amplification reaction. First, the polymerase has sufficient time to find the majority of primer-hybridized sites, resulting in an increase in the overall efficiency of each amplification cycle. Second, initiation sites for amplification will be governed by which annealing sites form the most stable primer-duplex rather than by which site has the greatest accessibility. This significantly improves the reproducibility of the pattern because the amplification sites are competing based on primer hybridization equilibria rather than on kinetic accessibility. Since relative equilibria are far less sensitive to small variations in temperature and ionic strength than are the relative kinetics of accessibility to a specific DNA site, the integrity of the resulting pattern is less sensitive to small variations of ionic stength and temperature. The increased efficiency of the amplification process makes it possible to generate a reproducible and easily detectable pattern within 25 amplification cycles for the RS amplification and 28 cycles for the RS/AG amplification.

The arbitrary priming procedures reported by Williams et al. and Welsh et al. both require a large number of amplification cycles, 45 and 32–42, respectively. Use of such a high number of amplification cycles frequently results in the formation of secondary amplification products and nonspecific DNA synthesis. A product profile background which contains high levels of such secondary amplification products and nonspecific DNA can severely restrict the ability of pattern recognition software to compare such a product profile with a known database. Use of fewer amplification cycles with 7–8 minute annealing times produces a far less complex product profile with a significantly reduced nonspecific DNA background. When the products from the RS or RS/AG amplifications are separated by electrophoresis the resulting pattern can be easily analyzed and processed by the types of pattern recognition software which are used for comparisons with a reference database.

GENERAL PROCEDURES

DNA Preparation

The bacterial cells are pelleted and then resuspended in lysis buffer (10 mM tris-HCl, 10 mM NaCl, 50 mM EDTA at pH 8.0). The cells are subjected to an enzymatic digest comprised of 25 U Lysostaphin, 30 ug N-Acetylmuramidase, 400 ug Achromopeptidase, and 600 ug Lysozyme in a final volume of 306 ul of lysis buffer. The digestion is carried out for 30–45 minutes at 37° C. Lysates are extracted with chloroform/phenol, then ethanol precipitated. The DNA is redissolved in a tris/EDTA buffer and the final concentration is determined by spectrophotometric measurement.

Amplification of DNA

An amplification reaction is generally described in Mullis et al., U.S. Pat. No. 4,683,195 and Mullis, U.S. Pat. No. 4,965,188, which patents are incorporated by reference. U.S. Pat. No. 4,683,195 is relevant for its teaching of the basic PCR approach, and U.S. Pat. No. 4,965,188 for its teaching of thermophilic polymerases. Specific conditions for amplifying a nucleic acid template are described in M. A. Innis and D. H. Gelfand, "PCR Protocols, A Guide to Methods and Applications", M. A. Innis, D. H. Gelfand, J.-J. Sninsky and T. J. White, eds. pp. 3–12, Academic Press (1989), which is incorporated by reference.

Specifically, Mullis is directed to a process for amplifying any desired specific nucleic acid sequence contained in a nucleic acid or mixture thereof. The process of Mullis comprises treating separate complementary strands of the nucleic acid with a molar excess of two oligonucleotide primers, and extending the primers to form complementary primer extension products which act as templates for synthesizing the desired nucleic acid sequence. The primers of Mullis are designed to be sufficiently complementary to different strands of each specific sequence to be amplified. The steps of the reaction may be carried out stepwise or simultaneously and can be repeated as often as desired (amplification is to be performed at least twice for the present invention).

In the context of the present invention, genomic DNA is isolated by cellular lysis and deproteinization. Amplification of the RS fragments (and arbitrary genomic regions if applicable) comprises annealing at least one pair of oligonucleotide primers to the highly conserved rDNA sequences (and to a plurality of arbitrary regions if applicable). In this procedure a nucleic acid polymerase and nucleotide triphosphates are introduced to the primers. The procedure is carried out under conditions suitable to amplify the RS fragments (and the arbitrary regions if applicable).

Preferred nucleic acid polymerases are DNA polymerases, particularly those which are thermostable. Preferred nucleoside triphosphates include deoxyribonucleoside triphosphates.

To facilitate identification of a microorganism from a pattern of amplification products generated from the genome of that organism, the pattern should contain elements common to all members of the species in conjunction with elements which differentiate the unique strains within that species. This attribute makes it possible to develop a species identification of a new strain, which is not contained within the reference pattern database, providing that the common elements of that species pattern are contained within the reference database. If different strains of the same species each generate completely unique patterns with no common species elements then the patterns themselves will not identify the species of an unknown strain.

Amplification of RS Fragments

DNA samples are diluted to a concentration of 20 ng/ul prior to amplification. A 1.25 ul aliquot of the bacterial genomic DNA is combined with 2.5 ul of 10× reaction buffer, 1 ul of a dNTP mixture (5 mM ea.), 1.25 ul each of two 15-base oligonucleotide primers (P1 and P2 at 50 ng/ul) and 42 ul of deionized water. (The primers are obtained from Research Genetics and are used without further purification. Other primers from other sources performing the same function may be used.) This mixture is heated to 94° C. for 5 minutes and 1.3 units of a thermophilic DNA polymerase is added to the mixture. Acceptable polymerases include Taq Polymerase, a thermostable DNA polymerase isolated from *Thermus aguaticus* YT1 according to a purification procedure developed by Cetus Corporation, and available from Perkin Elmer Cetus, Norwalk, Conn. Twenty-five amplification cycles are performed on an automated thermocycler. The cycle format is as follows: 1 minute at 94° C. (denaturing step); 2 minute ramp to 55° C.; 7 minutes at 55° C. (annealing step); 2 minute ramp to 72° C. and 2 minutes at 72° C. (synthesis step). The final cycle is followed by an additional 7 minutes at 72° C. to allow partial polymerizations to run to completion. At the end of the cycling program 1 ul of EDTA (0.5M) is added as a stop solution and the products are stored at 4° C.

Amplification of RS fragments and arbitrary genomic regions (RS/AG)

DNA samples are diluted to a concentration of 20 ng/ul prior to amplification. A 2.5 ul aliquot of the bacterial genomic DNA is combined with 5 ul of 10× reaction buffer, 2 ul of a dNTP mixture (5 mM ea.), 2.5 ul each of two 11-base oligonucleotide primers (P3 and P4 at 50 ng/ul) and 34 ul of deionized water. (The primers are obtained from Research Genetics and are used without further purification.) This mixture is heated to 94° C. for 5 minutes and 2.0 units of a thermophilic DNA polymerase is added to the mixture. Acceptable polymerases include Taq Polymerase, a thermostable DNA polymerase isolated from *Thermus aquaticus* YT1 according to a purification procedure developed by Cetus Corporation, and available from Perkin Elmer Cetus, Norwalk, Conn. Twenty-eight amplification cycles are performed on an automated thermocycler. The cycle format is as follows: 0.5 minutes at 94° C. (denaturing step); 2.75 minute ramp to 43° C.; 8 minutes at 43° C. (annealing step); 3.5 minute ramp to 72° C. and 2 minutes at 72° C. (synthesis step). The final cycle is followed by an additional 7 minutes at 72° C. to allow partial polymerizations to run to completion. At the end of the cycling program 1 ul of EDTA (0.5M) is added as a stop solution and the products are stored at 4° C.

Electrophoresis of Amplification Product

A 5 ul aliquot of the reaction mixture is removed and combined with 2 ul of loading buffer (15% Ficol, and 0.25% xylene cyanol). The mixture is loaded onto a 4% acrylamide/bis gel (29/1) and separated by electrophoresis. The gels are stained with ethidium bromide and are photographed on a UV transilluminator. Other techniques for visualizing the RS fragments and the AG fragments may be selected. One such popular alternative is the incorporation of fluorescence-labeled deoxynucleotides during amplification. Another alternative is spectroscopy.

EXAMPLES

FIGS. 2–6 were generated by carrying out amplification reactions using the procedure described in the section "Amplification of rDNA spacer regions" on genomic DNA samples from the specified bacteria. FIGS. 7–10 were generated by carrying out amplification reactions using the procedure described in the section "Amplification of rDNA spacer regions and arbitrary genomic regions" on genomic DNA samples from the specified bacteria. Amplification products were separated on an acrylamide gel and stained with ethidium bromide.

Bacteria representing eight different genera were chosen for amplification of RS fragments. Multiple species from the genera Listeria, and Staphylococcus, and multiple serotypes from the genus Salmonella were chosen since these represent a significant number of pathogenic microorganisms whose identification and characterization is particularly important. Five species were examined from the genus Escherichia and eight additional species taken were from four genera which are related to the pathogenic species of interest. Examples of the fragment size profiles produced in amplification reactions for these bacteria and resolved by electrophoresis are shown in FIGS. 2 through 6.

Bacteria representing five different genera were chosen for the combined amplification of the RS and AG fragments (RS/AG). Multiple serotypes and strains were chosen from the genera Listeria, and Staphylococcu S. Multiple serotypes were chosen from the genus Salmonella. Four strains were examined from the genus Escherichia and two strains taken from *Citrobacter freundii*. Examples of the fragment size profiles produced in amplification reactions for these bacteria and resolved by electrophoresis are shown in FIGS. 7 through 10. The size fragments which are common to both the RS and the RS/AG amplifications for each strain are indicated by arrows in the FIGS. 7–10.

The lanes containing amplifications of bacterial DNA are numbered in each figure and the strain number corresponding to that lane is given in the Figure legend. The unnumbered lanes contain time markers which are used to assign sizes to the amplification products. The sizes of the time markers are as follows: 228, 412, 693, 1331, and 2306 base pairs (bp). The sizes of the fragments produced in the amplifications were calculated from the positions of these fragments relative to the time markers. The uncertainty in the calculated sizes of the amplification products is approximately 2%.

Example 1

Figure 2:
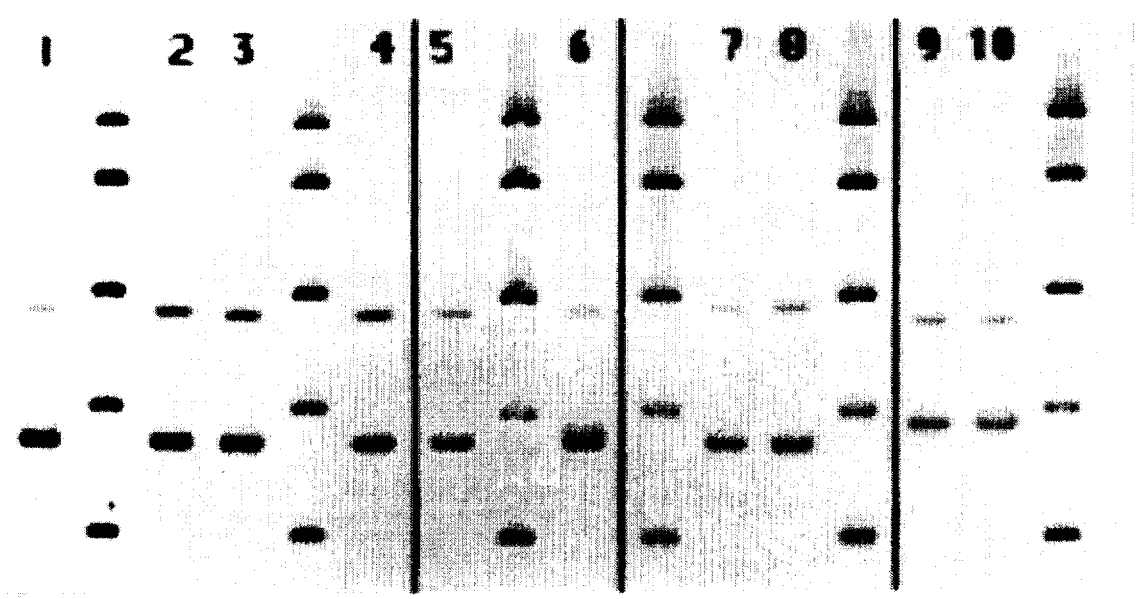
FIG. 2 is the visualized pattern for the amplification products of the spacer region in the rRNA genetic locus for four species from the genus Listeria including *Listeria monocytogenes*.

FIG. 2 shows the pattern for the amplification of RS fragments for four species from the genus Listeria. Lanes 1–4 show the patterns for four strains of *Listeria monocytogenes*. All four strains of *L. monocytogenes* show the same pair of fragments at 355 and 625 bp. The breakdown of remaining species of Listeria is as follows: lanes 5 and 6, *L. welshimeri* with fragments at 355 and 640 bp; lanes 7 and 8, *L. innocua* with fragments at 355 and 655 bp; lanes 9 and 10, *L. ivanovii* with fragments at 380 and 605 bp. There were no size fragments which were common to all species of Listeria.

Example 2

Figure 3:
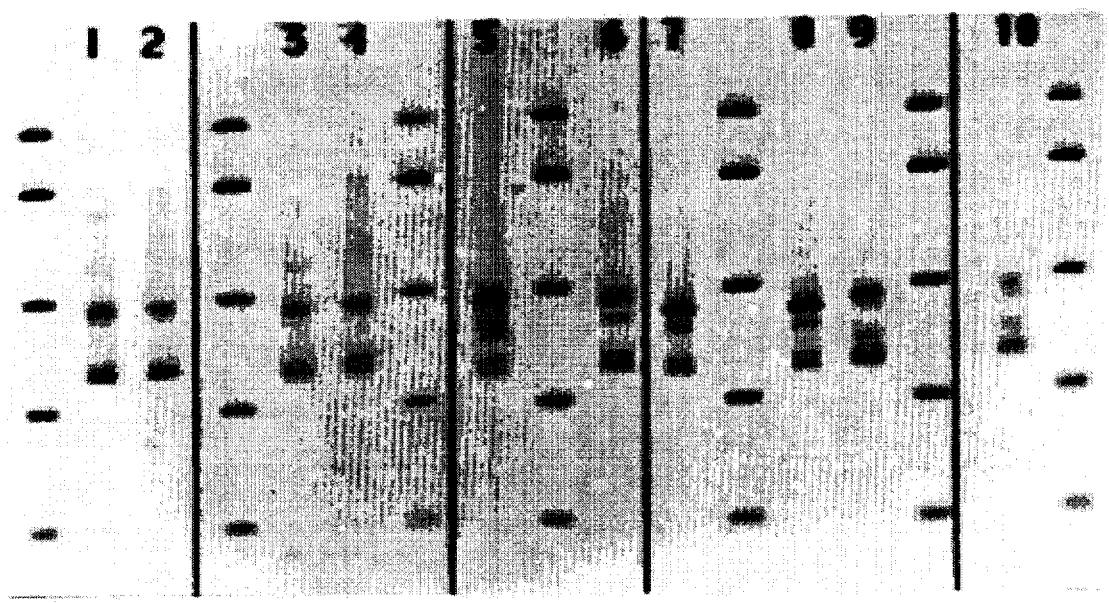
FIG. 3 is the visualized pattern for the amplification products of the spacer region in the rRNA genetic locus for four serotypes from the genus Salmonella including *Salmonella typhimurim*.

FIG. 3 shows the pattern for the amplification of RS fragments for four serotypes from the genus Salmonella. Patterns for four strains of *Salmonella typhimurim* are shown in lanes 1–4. All four strains of *S. typhimurim* show the same set of fragments at 480, 650, and 675 bp. The breakdown of remaining serotypes of Salmonella is as follows: lanes 5 and 6, both strains of *S. enteritidis* show common fragments at 480, 600, and 650 bp; lanes 7 and 8, both strains of *S. newport* show common fragments at 480, 570, and 610 bp and *S. newport* #707 also shows an additional fragment at 510 bp; lanes 9 and 10, both strains of *S. infantis* show common fragments at 495, 560, 630 and 655 bp. All the serotypes of Salmonella shown contain a common fragment in the region of 480–495 bp. However, all of the serotypes tested also contain unique product size profiles.

Example 3

Figure 4:
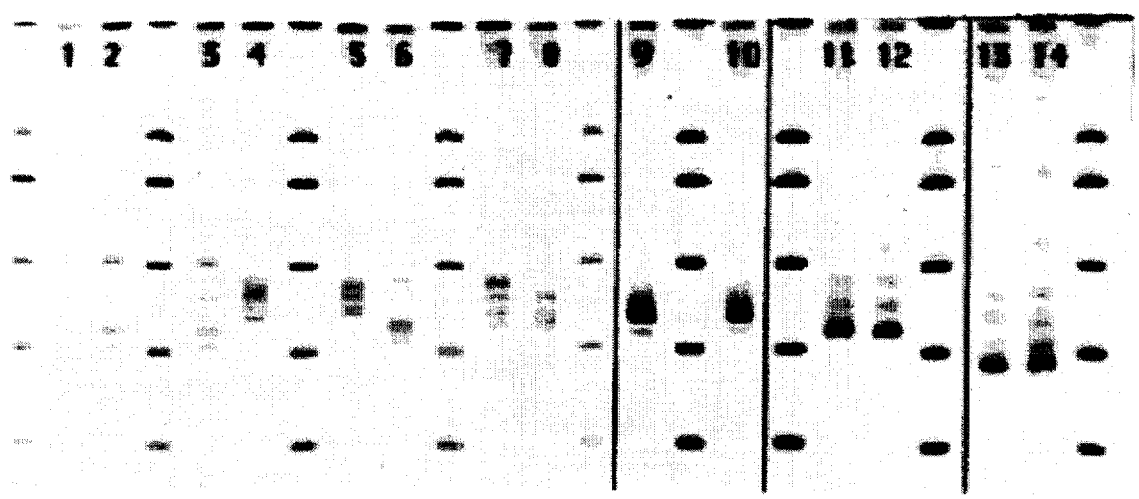
FIG. 4 is the visualized pattern for the amplification products of the spacer region in the rRNA genetic locus for five species from the genus Staphylococcus including *Staphylococcus aureus*.

FIG. 4 shows the pattern for the amplification of RS fragments for five species from the genus Staphylococcus. Patterns for eight strains of *Staphylococcus aureus* are shown in lanes 1–8. The strains in lanes 1–3 all show a common pattern with fragments of 425, 465, 565, and 705 bp. The remaining five strains found in lanes 4–8 show a series of diverse patterns with only a few elements in common, e.g., fragments of 485, 570 and 620 bp can be found in three of the five strains. However, no other size of fragments are common to more than two of the five strains. The remaining species of Staphylococcus are shown in lanes 9–16. The breakdown of these species is as follows: lanes 9 and 10, both strains of *S. scuiri* show common fragments at 345, 445 and 535 bp and *S. scuiri* #868 also shows an additional band at 530 bp; lanes 11 and 12, *S. warneri* with fragments at 455, 505, 525 and 545 bp; lanes 13 and 14, *S. saprophyticus* with fragments at 470, 550, and 640 bp; lanes 15 and 16, both strains of *S. epidermidus* show common fragments at 390 and 590 bp with *S. epidermidus* #796 showing an additional fragment at 520 bp and *S. epidermidus* #788 showing two additional fragments at 440 and 490 bp. The intraspecies variation in the pattern of amplification of RS fragments is far greater for *S. aureus* than for the other species of Staphylococcus which were evaluated. This is an example of a case where the information in the pattern generated by the amplification of RS fragments can differentiate below the level of species. Other than *Staphylococcus aureus* all the other species of Staphylococcus were characterized by the production of a single characteristic fragment which was present at a far greater level than the other amplification products. These characteristic fragments are as follows; *S. scuiri* at 345 bp, *S. warneri* at 505 bp, *S. saprophyticus* at 470 bp, and *S. epidermidus* at 390 bp. The intragenic variation in patterns found within the genus Staphylococcus is also significantly greater than the variation found in the genera of Salmonella and Listeria.

Example 4

Figure 5:
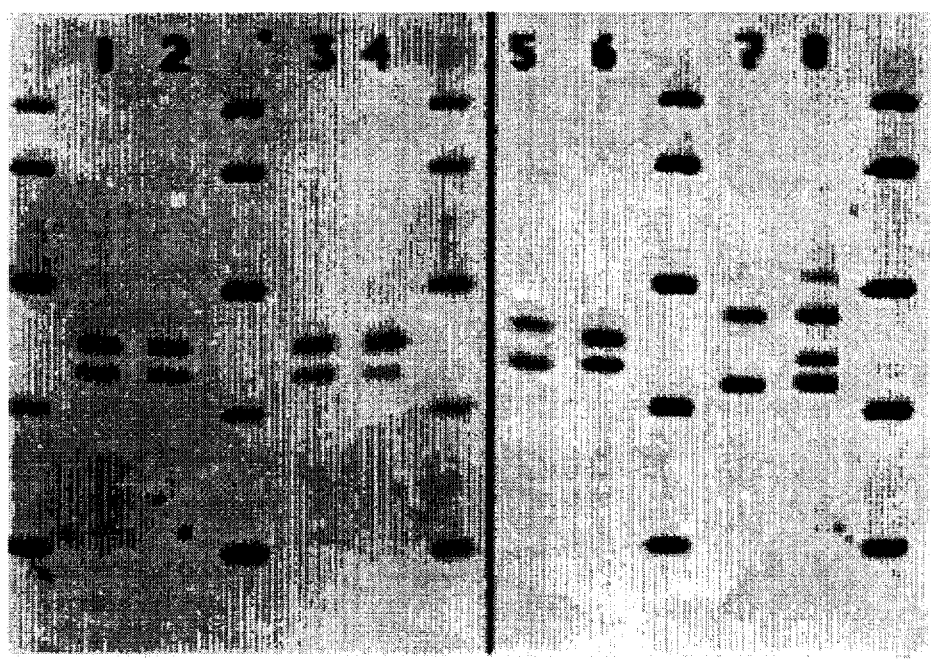
FIG. 5 is the visualized pattern for the amplification products of the spacer region in the rRNA genetic locus for five species from the genus Escherichia including *Escherichia coli*.

FIG. 5 shows the pattern for the amplification of RS fragments for five species from the genus Escherichia. Lanes 1–4 show the patterns for four strains of *Escherichia coli*. All four strains of *Escherichia coli* show the same pair of fragments at 480 and 530 bp. Single examples of four additional species of Escherichia are shown in lanes 5–8. None of these species appear to have any fragments in common with *Escherichia coli* although the *Escherichia fergusonii* in lane 6 does show a similar fragment size differential with fragments of 495 and 550 bp. There were no size fragments which were common to all species of Escherichia.

Example 5

FIG. 6 shows the pattern for the amplification of RS fragments for eight additional species taken from four genera which are related to the pathogenic species of interest. Lanes 1–4 show patterns for two species of Citrobacter. The two strains of *C. freundii* shown in lanes 1 and 2 both gave identical patterns with fragments of 315, 490, and 615 bp. The strains of *C. diversus* in lanes 3 and 4 also gave identical patterns with fragments of 460 and 615 bp. Lanes 5–10 show patterns for three species of Enterobacter. The two strains of *E. aerogenes* shown in lanes 5 and 6 yield similar patterns with a common fragment at 465 bp. The other two fragments are 280 and 590 bp for *E. aerogenes* #62. For *E. aerogenes* #167 a similar pattern of fragments each shifted 10 bases longer is seen. The two strains of *E. agglomerans* in lanes 7 and 8 show identical patterns with fragments of 450, 475 and 580 bp. In lanes 9 and 10 both strains of *E. cloacae* show fragments at 310, 465, and 580 bp. Lanes 11–14 show patterns for two species of Proteus. The two strains of *P. mirabilis* in lanes 11 and 12 show identical patterns with fragments at 505, 665 and 850 bp. In lanes 13 and 14 both strains of *P. vulgaris* show fragments 590, 840, 930, 1070, and 1200 bp. Lanes 15 and 16 show patterns for two strains of *Yersinia enterocolitica*. Both strains show a pair of fragments at 745 and 815 bp.

Example 6

FIG. 7 shows the pattern for the amplification of RS and AG fragments for three species from the genus Listeria. Lanes 1–4 show the patterns for four strains of *Listeria monocytogenes*. All four strains of *L. monocytogenes* show a common pair of fragments at 355 and 625 bp which are the same as the RS fragments observed in FIG. 2 for the same strains of *Listeria monocytogenes*. The remaining components in the pattern are the result of arbitrary genomic amplifications. These components distinguish three of the four *L. monocytogenes* strains. *L. monocytogenes* #891 and #899 generate the same amplification products. The breakdown of remaining species of Listeria is as follows: In lanes 5 and 6 *L. welshimeri* show a common pair of fragments at 355 and 640 bp which are the same as the RS fragments observed in FIG. 2 for the same strains of *L. welshimeri*. The remaining components in the pattern are the result of arbitrary genomic amplifications and can be used to distinguish between the two strains of *L. welshimeri*. In lanes 7 and 8, *L. innocua* show a common pair of fragments at 355 and 655 bp which are the same as the RS fragments observed in FIG. 2 for the same strains of *L. innocua*. The remaining components in the pattern are the result of arbitrary genomic amplifications and can be used to distinguish between the two strains of *L. innocua*.

Example 7

FIG. 8 shows the pattern for the amplification of RS and AG fragments for three serotypes from the genus Salmonella. Patterns for four strains of *Salmonella typhimurim* are shown in lanes 1–4. All four strains show a similar set of fragments at 480, 650, and 675 bp which are the same as the RS fragments observed in FIG. 3 for the same strains of *S. typhimurim*. The remaining components in the pattern are the result of arbitrary genomic amplifications. These components distinguish *S. typhimurim* #590 from the other three strains. The breakdown of remaining serotypes of Salmonella is as follows: In lanes 5 and 6 both strains of *S. infantis* show common fragments at 490, 560, 630 and 655 bp which are the same as the RS fragments observed in FIG. 3 for the amplifications of the same strains. The additional fragments, which are the result of arbitrary genomic amplifications, show similar patterns for both strains of *S. infantis*. In lanes 7 and 8, both strains of *S. enteritidis* show common fragments at 480, 600, and 650 bp which are the same as the RS fragments observed in FIG. 3 for the amplifications of the same strains. The additional fragments, which are the result of arbitrary genomic amplifications can be used to discriminate between these strains. All of the RS/AG patterns generated for the genus Salmonella were highly related. However, the individual Salmonella serotypes can be distinguished based on their unique product size profiles in the RS/AG amplifications.

Example 8

FIG. 9 shows the pattern for the amplification of RS and AG fragments for three species from the genus Staphylococcus. Patterns for four strains of *Staphylococcus aureus* are shown in lanes 1–4. The strain #807 in lane 1 shows fragments at 425, 465, 565, and 705 bp which are the same as the RS fragments observed in FIG. 4 for the same strain. The remaining components in the pattern are the result of arbitrary genomic amplifications. In lanes 2 and 3 *Staphylococcus aureus* #1098 and #1097 both show common fragments at 565, and 605 bp with #1098 showing an additional fragment at 505 bp and #1097 showing an additional fragment at 525 bp. All of these fragments are the same as the RS fragments observed in FIG. 4 for the same strains. The remaining components in the pattern are the result of arbitrary genomic amplifications and can be used to more easily distinguish between these two strains of *Staphylococcus aureus*. The strain #795 in lane 4 shows fragments at 470, 515, 565, and 610 bp which are the same as the RS fragments observed in FIG. 4 for the same strain. The remaining components in the pattern are the result of arbitrary genomic amplifications. The remaining species of Staphylococcus are shown in lanes 5–8. Both strains of *S. warneri*, #793 and #797, shown in lanes 5 and 6 exhibit fragments which correspond in size to the RS fragments observed for *S. warneri* in FIG. 4. The additional fragments, which are the result of arbitrary genomic amplifications can be used to discriminate between these strains. Both strains of *S. epidermidus*, #788 and #796, shown in lanes 7 and 8 exhibit fragments which correspond in size to the RS fragments observed in FIG. 4. The additional fragments, which are the result of arbitrary genomic amplifications can be used to discriminate between these strains.

Example 9

FIG. 10 shows the pattern for the amplification of RS and AG fragments for four strains from *Escherichia coli*. Lanes 1-4 show the patterns for four strains of *Escherichia coli*. All four strains of *Escherichia coli* show a pair of fragments at 480 and 530 bp which are the same as the RS fragments observed in FIG. 5 for the amplifications of the same strains. The remaining components in the pattern are the result of arbitrary genomic amplifications. These components can distinguish between all four strains of *Escherichia coli*. The two strains of *Citrobacter freundii* shown in lanes 5 and 6 both exhibit patterns which contain fragments of 315, 490, and 615 bp. These fragments correspond in size to the fragments produced in the RS amplification of *C. freundii* shown in FIG. 6. The additional fragments, which are the result of arbitrary genomic amplifications can be used to discriminate between these strains.

It is to be understood that the processes of the present invention may be modified according to practices of those skilled in the art without departing from the spirit and the scope of the invention herein.

---

We claim:

1. A method for the identification of the species, serotype and strain of a microorganism, comprising:

(a) isolating genomic DNA from the microorganism, said genomic DNA comprising variable sequences interspersed between highly conserved rDNA sequences in addition to arbitrary regions along the genome thereof;

(b) amplifying said variable sequences by annealing only a single pair of oligonucleotide primer of 10–12 bases in length to said highly conserved rDNA sequences at a temperature of about 43° to about 46° C. and during a period of about 5 to about 10 minutes, and introducing a nucleic acid ploymerase and nucleoside triphosphates to said primers, suitable to amplify said variable sequences, thereby producing ribosomal sequence fragments having particular distributions in size and number; and (c) amplifying said arbitrary regions by annealing as set forth in step (b) suitable to amplify said arbitrary regions, thereby producing arbitrary genomic fragments having particular distributions in size and number simultaneously with (b); and (d) separating said ribosomal sequence fragments and said arbitrary genomic fragments by size and analyzing the distribution of said ribosomal sequence fragments and said arbitrary genomic fragments both for elements common to all members of the species and for elements which differentiate the unique strains within that species only, and comparing to a database of previously visualized product thereby identifying the species, serotype and strain of the microorganism.

2. The method of claim 1 wherein said variable sequences are spacer regions.

3. The method of claim 1 wherein step (a) isolation comprises cellular lysis and deproteinization.

4. The method of claim 1 wherein said amplification is performed at least twice.

5. The method of claim 1 wherein the nucleic acid polymerase is a DNA polymerase and the nucleoside triphosphates are deoxyribonucleoside triphosphates.

6. The method of claim 5 wherein the DNA polymerase is thermostable.

7. The method of claim 1 wherein step (d) comprises resolving said ribosomal sequence fragments and said arbitrary genomic fragments by electrophoresis and thereafter visualizing said ribosomal sequence fragments and said arbitrary genomic fragments.

8. The method of claim 1 wherein the database contains fragment distributions which are characteristic for species, serotype and strain of *Listeria monocytogenes, Listeria innocua, Listeria ivanovii, Listeria welshimeri, Salmonella typhimurium, Salmonella enteritidis, Salmonella newport, Salmonella infantis, Staphylococcus aureus, Staphylococcus sciuri, Staphylococcus saprophyticus, Staphylococcus warneri, Staphylococcus epidermidus, Escherichia coli, Escherichia blattae, Escherichia fergusonii, Escherichia hermanii, Escherichia vulneris, Citrobacter freundii, Citrobacter diversus, Enterobacter aerogenes, Enterobacter agglomerans, Enterobacter cloacae, Proteus mirabilis, Proteus vulgari,* and *Yersinia enterocolitica.*

9. The method of claim 1 wherein in step (d) visualization is conducted by staining said ribosomal sequence fragments and said aribitrary genomic fragments with ethidium bromide or detecting the position of said ribosomal sequence fragments and said arbitrary genomic fragments by spectrophotometric procedures.

10. The method of claim 1 wherein in step (d) visualization is conducted by fLuorescence-labelling deoxynucleotide during amplification (b) and (c).

11. The method of claim 1 wherein said microorganism is bacteria.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAAGTCGTAA CAAGG                           15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAAGGCATCC ACCGT                           15

( 2 ) INFORMATION FOR SEQ ID NO:3:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAAGTCGTAA C                               11

( 2 ) INFORMATION FOR SEQ ID NO:4:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AAGGCATCCA C                               11